United States Patent [19]

Laties et al.

[11] Patent Number: 5,055,302

[45] Date of Patent: Oct. 8, 1991

[54] NEUROPEPTIDE CONTROL OF OCULAR GROWTH

[75] Inventors: Alan M. Laties, Philadelphia; Richard A. Stone, Havertown, both of Pa.

[73] Assignee: Trustees of the University of Pennsylvania, Philadelphia, Pa.

[21] Appl. No.: 483,447

[22] Filed: Feb. 22, 1990

[51] Int. Cl.$^5$ .................. A61F 2/00; A61K 37/00; A61K 37/02

[52] U.S. Cl. .................. 424/427; 424/422; 424/423; 424/428; 514/12; 514/21; 514/912; 514/929; 530/324; 530/843; 530/844

[58] Field of Search ............. 424/422, 427, 428, 423; 514/12, 21, 912, 929; 530/324, 843, 844

[56] References Cited

U.S. PATENT DOCUMENTS 3,862,927 1/1975 Said et al. ............... 530/324
4,745,100 5/1988 Gilbard et al. ........... 514/12

OTHER PUBLICATIONS

Increase in Retinal VIP After Eyelid Fusion in Primates, Stone et al., PNAS, , 257, 1988.
Different Effects of Substance P and VIP on the Motor Function of Bovine Intraocular Muscles, Suzuki et al., Invest. Ophthalmol. Vis. Sci., 24, 1566, 1983.

*Primary Examiner*—Thurman K. Page
*Assistant Examiner*—G. S. Kishore
*Attorney, Agent, or Firm*—Woodcock Washburn Kurtz Mackiewicz & Norris

[57] ABSTRACT

A method and composition for inhibition of abnormal postnatal ocular growth are disclosed. The composition comprises vasoactive intestinal peptide (VIP), PHI or a analogue of these peptides. The method for inhibition of abnormal postnatal ocular growth comprises administering to the eye of an animal effective amount of VIP, PHI or analogue of these peptides.

8 Claims, No Drawings

NEUROPEPTIDE CONTROL OF OCULAR GROWTH

REFERENCE TO GOVERNMENT SUPPORT

Portions of this invention were supported by National Eye Institute grant R01-EY-05454.

BACKGROUND OF THE INVENTION

This invention relates to control of ocular development and, more particularly, to the treatment of the eye to control the development of myopia (commonly known as nearsightedness).

It has been estimated that about one of every four persons on earth suffers from myopia. About one-half or more of these cases are axial myopia, i.e., an elongation of the eye along the visual axis.

At birth, the human eye is about two-thirds adult size and is even at that size relatively short in the axial direction. As a consequence, young children tend to be farsighted. During childhood, as the eye grows, there is a compensatory fine tuning of the optical properties of the cornea and lens to the increasing ocular length. Often the entire process is virtually perfect such that no correction is needed for sharp vision of a distant object; the eye is emmetropic. When regulatory failure in this finely tuned process occurs, it usually goes toward a lengthened eye. As a result, distant images focus in front of the plane of the retina and axial myopia results. If, on the other hand, the regulatory failure leads to an eye whose ocular length is too short, near images would focus behind the plane of the retina and the result is hyperopia (commonly known as farsightedness).

Over the years, many theories have been put forth to explain the development of myopia, e.g., inheritance, excessive near work, and environmental influences such as hours of sunshine, diet, etc. From these theories many preventative measures have been proposed including spectacles, eye exercise, eye rest, cycloplegics, and other drug therapies. The clinical literature on the subject is both massive and inconclusive.

There is now substantial evidence to link the posterior part of the eye, specifically image quality at the retina, to the postnatal regulation of ocular growth. There is significant experience of myopia resulting in an eye that is subjected to retinal images of poor quality. Axial myopia can be experimentally induced, in either birds or primates, in an eye in which the retina is deprived of formed images, e.g., by suturing the eyelids or wearing an image-diffusing goggle. The experimental myopia induced in primates such as monkeys precisely mimics the common axial myopia of humans.

Thus, the phenomenon of an animal's vision process apparently contributes to the feedback mechanism by which postnatal ocular growth is normally regulated and refractive error is determined. This indicates that this mechanism is neural and likely originates in the retina.

Studies reported in Stone et al. (1988) Proc. Natl. Acad. Sci. 85: 257-260, revealed that there is an increase in retinal vasoactive intestinal peptide after eyelid fusion in primates. In all animals, the immunohistochemical reactivity of the retina for vasoactive intestinal peptide was much higher in the closed than in the open eyes.

In the application of R. A. Stone, A. M. Laties and P. M. Iuvone, U.S. application Ser. No. 342,942, filed Apr. 25, 1989, which is a continuation-in-part of Ser. No. 202,220, filed June 3, 1988, method of controlling the abnormal postnatal growth of the eye of a maturing animal was found which comprises controlling the presence of a neurochemical, by agonist therapy, which neurochemical is found to be changed under conditions during maturation leading to abnormal axial length. Therein it is disclosed that in experimental animals, such as chicks or monkeys, subjected to ocular image deprivation ordinarily leading to the development of myopia, the metabolism of certain retinal neurochemicals is altered leading to changes in retinal concentrations thereof. Specifically, retinal concentrations of dopamine were found to be reduced during such image deprivation and the ocular administration of a dopamine-related agent, e.g., apomorphine, a dopamine agonist, was found to inhibit or actually prevent the axial enlargement of the eye under conditions ordinarily leading to such enlargement.

In the application of A. M. Laties and R. A. Stone, U.S. application Ser. No. 369,293, filed June 21, 1989, is described a method of controlling the abnormal postnatal growth of the eye of a maturing animal by the administration of effective amounts of a muscarinic pharmacological agent known to be effective in brain neural tissue and/or neural ganglia, e.g., a muscarinic antagonist such as pirenzepine. Also described therein is the use of a cholinergic agonist such as carbamyl choline for inducing axial growth of the eye of a maturing animal.

SUMMARY OF THE INVENTION

The present invention provides methods and compositions for regulating the growth of an animal's eye. The methods of the invention comprise administration of an effective amount of the neuropeptides vasoactive intestinal peptide, PHI, or analogues of these peptides to the eye of the animal. This invention is more particularly pointed out in the appended claims and is described in its preferred embodiments in the following description.

DETAILED DESCRIPTION OF THE INVENTION

In the ordinary visual function of the eye of an animal, light forming an image passes through the lens and is received by the retina, a neural tissue embryologically related to the brain. The retina transmits this information to the optic nerve which sends it on to the brain.

Without wishing to be bound to any particular theory or mode of action, it is believed that the compositions and method of the invention act on the eye through the retina. Retinal neurochemicals (i.e., neuro-active chemical compounds) are key ingredients in the vision process. Specifically, light forming the image is sensed by the light receptors, the rods and cones, of the retina. These photoreceptors act as transducers changing light energy into electrical and/or chemical signals.

In the regular process of transmitting the image information to the brain, retinal nerve cells release neurochemicals to pass information to adjacent retinal cells as parts of networks in the retina leading to the formulation and qualities of the signals that later go to the brain via the optic nerve.

In accordance with this invention, it has been found that administration of an effective amount of the neuropeptide vasoactive intestinal peptide (hereinafter VIP) can be effective in blocking the axial-elongation myopia ordinarily produced by ocular image deprivation in a chick experimental model. Inhibition of axial elongation of the eye in the chick model is unexpected, as elevated levels of VIP have been reported in primates having experimentally induced myopia. In the only relevant prior experience, inhibition of myopia development followed treatment that went in the opposite sense, i.e., it followed replenishment or replacement of a deficiency. Whereas in the present instance, assuming the monkey observations are transferable to the chick, VIP therapy in effect adds to a reservoir already full. In fact then, based on prior experience the opposite effect, axial elongation of the eyeball, would be suggested by the addition of VIP to the eye.

In the performance of the method of the invention, VIP, PHI or ocular growth inhibiting analogues thereof may be administered to the animal. Porcine VIP has the amino acid sequence His-Ser-Asp-Ala-Val-Phe-Thr-Asp-Asn-Tyr-Thr-Arg-Leu-Arg-Lys-Gln-Met-Ala-Val-Lys-Lys-Tyr-Leu-Asn-Ser-Ile-Leu-Asn-NH$_2$. VIP has been isolated from a number of species, including human, porcine and bovine species. The peptide has the same amino acid sequence in these three species, however, the amino acid sequence may be different in other species. VIP from any source is suitable for use in the method of the invention.

VIP may be prepared by isolation from tissue containing the peptide, such as intestinal tissue by the method in Said U.S. Pat. No. 3,880,826 which is hereby incorporated by reference as if fully set forth herein. VIP may also be prepared by recombinant DNA techniques such as the method in Itoh et al. (1983) Nature 304, 547-549. Additionally, VIP is available from commercial sources such as Peninsula Laboratories, Inc., Belmont, California and Sigma Chemical Company, St. Louis, Mo., or it can be chemically synthesized using commercially available reagents.

PHI is a twenty-seven amino acid peptide closely related in amino acid sequence and activity to VIP. The amino acid sequence of this peptide may vary from species to species. Porcine PHI has the amino acid sequence His-Ala-Asp-Gly-Val-Phe-Thr-Ser-Asp-Phe-Ser-Arg-Thr-Leu-Gly-Gln-Leu-Ser-Ala-Lys-Lys-Tyr-Leu-Glu-Ser-Leu-Ile-NH$_2$. Human PHI, designated PHM-27 differs from porcine PHI by two amino acids. PHM-27 has the amino acid sequence His-Ala-Asp-Gly-Val-Phe-Thr-Ser-Asp-Phe-Ser-Lys-Leu-Leu-Gly-Gln-Leu-Ser-Ala-Lys-Lys-Tyr-Leu-Glu-Ser-Leu-Met-NH$_2$. As used herein the term PHI includes peptides from whatever species that are analogous to porcine PHI whether or not the amino acid sequence is the same as that of porcine PHI. PHI is available from commercial sources such as Peninsula Laboratories, Inc., Belmont, Calif., and Sigma Chemical Company, St. Louis, Mo. PHI may also be chemically synthesized using commercially available reagents. Human PHM-27 may be prepared using recombinant DNA techniques according to the method of Itoh et al. supra.

VIP and PHM-27 are formed in vivo in humans from the same precursor polypeptide, see Itoh et al. supra, all or a portion of this precursor molecule may also be suitable for use in the invention. The precursor molecule may be produced according to the method of Itoh et al supra.

Analogues of VIP and PHI having ocular growth inhibiting activity that are suitable for use in the invention include peptides having substantially the same amino acid sequence as VIP or PHI, i.e. peptides having more or fewer amino acids than VIP or PHI and peptides having one or more amino acid substitutions. Other suitable analogues of VIP and PHI include fragments of VIP or PHI; amino acid sequences joined by bonds other than peptide bonds; peptides modified by the addition of molecules other than amino acids and peptides modified by the substitution of amino acids with molecules other than amino acids. Molecules that resemble peptides in their binding/activation qualities at the receptor site to which VIP generally binds are also within the scope of the invention.

It is preferred that the VIP, PHI or analogue used in any particular embodiment of the invention be isolated or derived from the same species to which it will be administered to ensure effectiveness and to avoid or reduce adverse reactions to the peptide. However, because the structure of VIP is the same in humans and porcine and bovine species, it may be possible to administer VIP from one species to a different species with minimal adverse reactions.

VIP, PHI or ocular growth inhibiting analogues may be administered to the eye by topical application or injection into the conjunctival tissue of the eye.

VIP, PHI and ocular growth inhibiting analogues are preferably administered to the eye in combination with a pharmaceutically acceptable carrier or diluent and optionally a preservative. Suitable carriers or diluents include saline solution, various buffer solutions, cyclodextrins and other protective carriers or complexes, glycerol and prodrug formulations. VIP, PHI and analogues may be administered to the animal alone or in combination with each other; for example, VIP and PHI, or PHI and an analogue. VIP, PHI or analogue may also be combined with other pharmaceutical agents such as dopaminergics, adrenergics, cholinergics or growth factors for administration to the eye. The amount of VIP, PHI or analogue administered will vary according the species of the individual, the amount of orbital tissue present in the eye and the distance the peptide will have to diffuse from the site of administration, and the penetrability of the eye.

Administration of VIP, PHI and ocular growth inhibiting analogues to reduce axial elongation of the eyeball found in myopia is expected to be effective in inhibiting the progression of myopia in mammalian species, including humans, and avian species. VIP, PHI and ocular growth inhibiting analogues are administered to the eye of the animal for a length of time effective to inhibit axial ocular elongation and thus reduce or stop the progression of myopia in the animal. In humans, for example, the vision of a child would be tested at intervals. If the child were near-sighted or if near sight were impending, VIP, PHI or analogue would be administered to the child for a length of time during the growth period of the eye effective to inhibit axial elongation of the eye. The effectiveness of the VIP, PHI or analogue in inhibiting axial elongation is determined by repeated testing the child's eyes at suitable intervals. An improvement or stabilization of the child's refractive state indicates that inhibition of axial elongation has occurred. Depending on the individual case, VIP, PHI or analogue may be administered indefinitely or until such time as vision has stabilized and myopia does not appear to be progressing. At the present time, since the progression of myopia ceases during the second decade of life, it is believed that once the propensity for eye growth has ceased at maturation (age 18-24), administration of VIP, PHI or analogue may be discontinued.

EXAMPLE

Form deprivation myopia in day-old White Leghorn chicks was induced by eyelid suture under aseptic conditions and ether anesthesia. One eyelid of the chicks was sutured. Closure of the eyelid does not block vision. Translucent vision is permitted through the eyelid. The contralateral unsutured open eye served as the control eye. VIP was administered daily to the deprived, or sutured, eye. Saline was administered to the unsutured eye. All agents were given under ether anesthesia by subconjunctival injection. The chicks were maintained on a 12 hour light/dark cycle. The birds were killed at ages up to 4 weeks by decapitation under deep pentobarbital anesthesia. Axial and equatorial dimensions of unfixed eyes were measured with vernier calipers.

VIP (porcine VIP, Peninsula Laboratories, Inc. Belmont Calif.) was administered in three (descending) dose levels to lid-sutured eyes of 23 chicks and to one eye of an additional 15 chicks which had both eyes open. A profound treatment effect significant at the $p<0.001$ level was found for VIP at the 0.25 µg dose in birds with sutured eyelids. At this dose there was an approximately an 80% block of axial elongation in the experimental myopia model lid-sutured eyes. Importantly, at all three levels of VIP application, there was no significant treatment effect in the controls (both eyes open) either on axial or equatorial diameters. On the basis of these laboratory findings, it is apparent that the neuropeptide VIP can inhibit the axial elongation of the chick eye in this model of experimental myopia.

| Effect of VIP on growth of lid-sutured eyes. Ocular dimensions (means ± S.E.M.) (deprived minus control eye) | | | |
|---|---|---|---|
| Drug n | Daily dose (µg) | Axial length (mm) | Equatorial diameter (mm) |
| VIP 5 | 2.5 | 0.34 ± 0.15 | 0.90 ± 0.10 |
| VIP 9 | 0.25 | 0.07 ± 0.07* | 0.92 ± 0.04 |
| VIP 9 | 0.025 | 0.17 ± 0.10* | 0.91 ± 0.05 |
| saline 32 | — | 0.35 ± 0.03 | 0.84 ± 0.05 |

By one way analysis of variance, significant treatment effects on axial length are identified for VIP at dose of 0.25 µg ($p<0.001$) and at 0.25 µg ($p<0.05$). The equatorial diameters have no significant treatment effects with VIP treatment. VIP at a daily dose of 2.5 µg is outside the effective range of the peptide.

| Effect of VIP on growth of open eyes Ocular dimensions (means ± S.E.M.) (treated eye minus untreated eye) | | | |
|---|---|---|---|
| Drug n | Daily dose (µg) | Axial length (mm) | Equatorial diameter (mm) |
| VIP 5 | 2.5 | 0.13 ± 0.06 | −0.01 ± 0.06 |
| VIP 10 | 0.25 | 0.03 ± 0.05 | 0.02 ± 0.02 |
| VIP 9 | 0.025 | 0.008 ± 0.10 | 0.07 ± 0.04 |

We claim:

1. A method of controlling the postnatal growth tending to lead to myopia of the eye of a maturing animal in whom eye growth is not yet complete, which comprises ocular administration of an amount of a compound selected from the group consisting of vasoactive intestinal peptide, PHI and ocular growth inhibiting analogues of vasoactive intestinal peptide and PHI effective to inhibit postnatal axial growth of the eye tending to lead to myopia.

2. The method of claim 1 wherein said compound is vasoactive intestinal peptide.

3. The method of claim 1 wherein said compound is an ocular growth inhibiting analogue of VIP or PHI having substantially the same amino acid sequence as VIP or PHI.

4. The method of claim 1 wherein said compound is an ocular growth inhibiting compound that mimics the growth inhibiting effect of VIP, PHI or ocular growth inhibiting analogue of VIP or PHI on the eye.

5. A method of inhibiting the postnatal axial growth which tends to lead to myopia of the eye of a maturing animal in whom eye growth is not yet complete ordinarily leading to said growth, which comprises administering to said eye during postnatal maturation an effective amount of a compound selected from the group consisting of vasoactive intestinal peptide, PHI and ocular growth inhibiting analogues of vasoactive intestinal peptide and PHI.

6. The method of claim 5 wherein said compound is vasoactive intestinal peptide.

7. The method of claim 5 wherein said compound is an ocular growth inhibiting analogue of VIP or PHI having substantially the same amino acid sequence as VIP or PHI.

8. The method of claim 1 wherein said compound is an ocular growth inhibiting compound that mimics the growth inhibiting effect of VIP, PHI or ocular growth inhibiting analogue of VIP or PHI on the eye.

* * * * *